(12) United States Patent
Vajinepalli et al.

(10) Patent No.: US 10,231,694 B2
(45) Date of Patent: Mar. 19, 2019

(54) AUTOMATIC BLOOD VESSEL IDENTIFICATION BY NAME

(71) Applicant: KONINKLIJKE PHILIPS N.V., Eindhoven (NL)

(72) Inventors: Pallavi Vajinepalli, Bangalore (IN); Rajendra Singh Sisodia, Bangalore (IN); Lalit Gupta, Bangalore (IN); Ganesan Ramachandran, Bangalore (IN); Celine Firtion, Bangalore (IN); John Petruzzello, Carmel, NY (US); Ajay Anand, Fishkill, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 36 days.

(21) Appl. No.: 14/364,483

(22) PCT Filed: Dec. 7, 2012

(86) PCT No.: PCT/IB2012/057057
§ 371 (c)(1),
(2) Date: Jun. 11, 2014

(87) PCT Pub. No.: WO2013/088320
PCT Pub. Date: Jun. 20, 2013

(65) Prior Publication Data
US 2014/0343431 A1 Nov. 20, 2014

Related U.S. Application Data

(60) Provisional application No. 61/576,551, filed on Dec. 16, 2011.

(51) Int. Cl.
*A61B 8/00* (2006.01)
*A61B 8/06* (2006.01)
(Continued)

(52) U.S. Cl.
CPC .............. *A61B 8/06* (2013.01); *A61B 8/0866* (2013.01); *A61B 8/0891* (2013.01); *A61B 8/466* (2013.01);
(Continued)

(58) Field of Classification Search
USPC .......................................... 600/454
See application file for complete search history.

(56) References Cited

U.S. PATENT DOCUMENTS

| 6,068,597 A * | 5/2000 | Lin ...................... A61B 5/0051 600/443 |
| 6,511,427 B1 * | 1/2003 | Sliwa, Jr. ............. A61B 5/4869 600/438 |

(Continued)

FOREIGN PATENT DOCUMENTS

| CN | 102078202 A | 6/2011 |
| JP | 2002224114 A | 8/2002 |

(Continued)

OTHER PUBLICATIONS

Christiaens et al (Three-dimensional power Doppler imaging: volume reconstruction of pulmonary artery flow with an in vitro pulsatile flow system, 1997).*

(Continued)

*Primary Examiner* — Joel F Brutus

(57) ABSTRACT

A device is configured for interrogating a blood vessel to derive flow characteristics (S628) and for, responsive to the deriving and based on the derived characteristics, anatomically identifying the vessel. A spatial map of the vessels may be generated based on the interrogating, and specifically the Doppler power computed from data acquired in the interrogating. Subsequent interrogating (S668) may occur, based on the map and on a user-selected set of vessels and/or vessel categories, to derive clinical Doppler indices. The device can be designed to automatically set a sample volume (509)

(Continued)

for the subsequent interrogating, and to operate automatically from the user selection to display of the indices. The display may further include an image (524) of the vessels summoned by the set, annotated by their individual anatomical names, and optionally a diagnosis relating to blood flow. The displayed image may be enlarged to zoom in on the user's onscreen selection. The device may feature a two-dimensional ultrasound non-phased array of transducer elements.

22 Claims, 6 Drawing Sheets

(51) Int. Cl.
*A61B 8/08* (2006.01)
*A61B 8/02* (2006.01)
*G01S 7/52* (2006.01)

(52) U.S. Cl.
CPC .............. *A61B 8/468* (2013.01); *A61B 8/488* (2013.01); *A61B 8/5223* (2013.01); *A61B 8/02* (2013.01); *A61B 8/467* (2013.01); *F04C 2270/041* (2013.01); *G01S 7/52073* (2013.01)

(56) References Cited

U.S. PATENT DOCUMENTS

| 6,682,483 | B1 | 1/2004 | Abend | |
|---|---|---|---|---|
| 2003/0013958 | A1* | 1/2003 | Govari | A61B 5/0422 600/437 |
| 2003/0125624 | A1* | 7/2003 | Shiki | A61B 8/06 600/443 |
| 2004/0019278 | A1* | 1/2004 | Abend | G01S 7/52026 600/454 |
| 2006/0100530 | A1* | 5/2006 | Kliot | A61B 5/0002 600/483 |
| 2006/0239540 | A1* | 10/2006 | Serra | A61B 8/14 382/154 |
| 2008/0119736 | A1* | 5/2008 | Dentinger | A61B 8/02 600/455 |
| 2009/0326379 | A1 | 12/2009 | Daigle et al. | |
| 2010/0128963 | A1* | 5/2010 | Waku | A61B 5/0073 382/134 |
| 2010/0249597 | A1 | 9/2010 | Shi | |
| 2011/0034807 | A1 | 2/2011 | Yoo | |

FOREIGN PATENT DOCUMENTS

| JP | 2009022342 A | 2/2009 |
|---|---|---|
| WO | 2011021175 A2 | 2/2011 |
| WO | 2011041244 A1 | 4/2011 |
| WO | 2012085788 A2 | 6/2012 |
| WO | 2013088314 A1 | 6/2013 |

OTHER PUBLICATIONS

Tarzamni et al (Nomograms of Iranian fetal middle cerebral artery Doppler waveforms and uniformity of their pattern with other populations nomograms).*

Niemeijer et al (Automatic classification of retinal vessels into arteries and veins).*

Pallavi, V. et al "Doppler Based Identification of Uterine Artery and Umbilical Artery for Monitoring Pregnancy", 2010 Annual International Conf. of the IEEE Engineering in Medicine and Biology Society, pp. 6300-6303.

* cited by examiner

AUTOMATIC BLOOD VESSEL IDENTIFICATION BY NAME

CROSS-REFERENCE TO PRIOR APPLICATIONS

This application is the U.S. National Phase application under 35 U.S.C. § 371 of International Application No. PCT/IB2012/057057, filed on Dec. 7, 2012, which claims the benefit of U.S. Provisional Patent Application No. 61/576,551, filed on Dec. 16, 2011. These applications are hereby incorporated by reference herein.

FIELD OF THE INVENTION

The present invention is directed a device for interrogating to identify a blood vessel and more particularly, for identifying the vessel anatomically.

BACKGROUND OF THE INVENTION

Assessing the well being of fetus is a very important clinical practice in pregnancy care. Currently, the most prevalent ways for doctors to assess fetal well-being are the analysis of fetal heart rate using a cardio-tocograph (CTG) and the assessment of maternal and fetal blood vessel flows using ultrasound Doppler. Ultrasound Doppler waveform analysis of specific blood flows of fetus and mother is part of established medical practice, and a standard recommendation in various clinical guidelines for the diagnosis and assessment of high-risk pregnancies (type-2 diabetes, hypertension or pre-eclampsia in mother and IUGR—intra-uterine growth restriction of fetus). One of the main aims of routine antenatal care is to identify the "at risk" fetus in order to clinically intervene, thereby reducing the incidence of perinatal morbidity and mortality. Some of the vessels useful in the assessment of fetal well-being are: the umbilical artery, the middle cerebral artery, the ductus venosus, and the (left and right) uterine arteries and umbilical veins.

Ultrasound scanners have become indispensible in the monitoring of pregnancies worldwide. They currently provide the best option to monitor the growth and development of the fetus. Duplex ultrasound scanners provide ultrasound pulsed wave Doppler in addition to the regular scan. Color and power Doppler are newer additions to the range of scanners that provide for vascular imaging. Color Doppler, in particular, is commonly provided, resulting in what is often called a "triplex" scanner. In a 2D color flow mapping, the spatial image of the vessels is overlaid with the flow image such that the ultrasound reflection is represented in gray scale and the flow velocity information is rendered in color.

Doppler exams typically require a great degree of skill to obtain a clinically useful measurement. For example, correct orientation of the probe with respect to the vessel is essential to ensure that the beam-flow angle is less than 60 degrees. Errors in measurements are amplified when angles of greater than 60 degrees are used in the determination of velocities. The standard workflow on a clinical ultrasound scanner allows a sonographer to determine the orientation of the probe with respect to the vessel using a standard B-mode and Color Flow display. The spectral Doppler measurements are then obtained thus ensuring that the measured velocities are correct.

Also, currently the sample volumes are manually set by radiologists which requires skill.

The use of ultrasound in vascular applications to perform Doppler velocimetry requires availability of skilled personnel.

Duplex ultrasound scanners are used to measure the rate of flow in blood vessels and to produce spectrograms representative of the blood flow. Measurements can be made based on the spectrogram to yield Doppler indices used by the physician in rendering a medical diagnosis. The blood vessel by which the diagnosis is to be made is, via the display, identified anatomically by its name.

U.S. Patent Application 2011/0034807 to Yoo et al. discloses an ultrasound system for automatically labeling vessels in the sense of marking an imaging-wise segmented vessel with a number or color to differentiate it from another segmented vessel.

SUMMARY OF THE INVENTION

In emerging market countries such as India, the shortage of specialists limits the availability and access to ultrasound. Hence, an automated method of acquiring and evaluating Doppler signals for clinical diagnosis (without requiring the user to interpret an ultrasound scan image) would be useful to non-radiologists such as OB/GYN or cardiologists who are the primary treatment providers.

In addition, a low-cost system is essential to provide an attractive solution in emerging market environments. Devices that are currently available in the market for antenatal check-ups and labor are the ultrasound and CTG machines. However, both of these devices are relatively expensive.

Also, a complicating factor in trying to automated pregnancy monitoring is that a very large region of insonation is generated, having for example a depth range from 2 to 10 centimeters (cm). This region may possibly have many blood vessels. The common iliac artery branches into the external iliac artery and internal iliac artery. The internal iliac artery branches into the uterine artery and obturator artery. The uterine artery continues as the cervical artery and vaginal artery, while the external iliac branches into the femoral and epigastric arteries. Any one of these peripheral arteries could be present in the spatial region being interrogated while looking for the uterine or external iliac arteries.

A further consideration is that the patient's movement, or movement of the fetus in obstetric applications, can adversely impact identification of the vessel of interest. This factor increases with the time needed to perform the examination.

There exists a need for a low-cost, easy-to-use, and time-saving solution to provide Doppler velocimetry to screen for and monitor high risk pregnancies.

Commonly-assigned patent application entitled "Automated Doppler Velocimetry Using a Low-Cost Transducer" discloses a hand-held, stand-alone, Doppler-based, ultrasound probe whose examining face is less finely divided into separate transducer elements, i.e., for relatively few separate elements. As mentioned therein, the probe operates automatically without the need for interpreting a visual display of anatomy.

The present patent application relates to automatically and anatomically identifying all blood vessels having more than a minimum size in a region of insonation and to automatically labeling them, with particular application to the probe referred to immediately above.

In accordance with the present invention, a device is configured for interrogating a blood vessel to derive flow characteristics of the vessel and for, responsive to the deriving and based on the derived characteristics, anatomically identifying the vessel.

In an aspect, the device is further configured for generating a spatial map of blood vessels, the above-mentioned vessel being among the vessels.

In a sub-aspect, the device is further configured for the interrogating based on the map and responsive to the generating.

In another sub-aspect, in generating the map, the device selectively evaluates a voxel based on Doppler power detected by a single transducer element of the device.

From another standpoint, the device is configured for interrogating vessels to respectively derive flow characteristics and for, responsive to the respective deriving and based on the respectively derived characteristics, anatomically identifying the vessels individually, with the aforementioned vessel being among those interrogated.

The device, in a sub-aspect, is further configured for, based on a result of the interrogating, generating a spatial map of vessels from among the vessels interrogated.

As a further sub-aspect, the device is further configured for, based on the map and responsive to said generating, setting a sample volume.

From an alternative standpoint, the interrogating is based on a map of the vessels and responsive to generation of the map.

In some embodiments, the interrogating based on the map is applied to all of the vessels in the map.

In a different sub-aspect, the device includes a user display and is further configured for, responsive to the identifying of the vessels, generating for viewing, on the display, a summary of the identified vessels. The summary includes names of the identified vessels and information obtained by the deriving of the characteristics.

In a related sub-aspect, the device includes a user interface that further includes a display. An identified vessel is presented for selection via the interface. The device is further configured for, based on a map generated based on the interrogating of vessels, displaying, on the display, an image of the selected vessel and its anatomical name.

In one other related sub-aspect, the device includes a user interface that includes a display. The device is configured for, responsive to the identifying of the vessels, generating for viewing, on the display, a map from which the identifying was performed. The device is further configured for, responsive to user selection, via the interface, of one or more vessels of the map, zooming in on the one or more selected vessels onscreen.

In yet one other related sub-aspect, the device includes a user interface by which a set containing multiple ones of the identified vessels is selectable for the identifying of the vessels. Also, the device may be further configured for, based on the selection, anatomically identifying, to a user, the multiple ones of the identified vessels concurrently.

With regard to selectability, in a further sub-aspect, the device is further configured for, based on a map of vessels from among the plural vessels and responsive to the selecting, setting a sample volume.

In a general sub-aspect, the identifying identifies the vessel individually by anatomical name, rather than just by vessel category.

From another general standpoint, a handheld, stand-alone, diagnostic apparatus may incorporate the device.

As another applicable feature, the device comprises transducer elements and is configured not to collectively use any of the elements to focus, nor to steer, a beam used in the interrogating.

In a particular sub-aspect, the device is further configured for determining whether periodic pulsatile motion exists in both a positive-flow channel and a negative-flow channel of an artery. The identifying is based on the determination.

In one additional sub-aspect, the device is further configured for the identifying being based on a ratio between time to peak systole and time from peak systole to end diastole.

In a different, complementary sub-aspect, the characteristics serve as features in multidimensional feature space, with the identifying being based on proximity in the space.

In a different but related sub-aspect, the identifying includes computing a time span of a spectrogram, and a number of peaks in a maximum frequency envelope of the spectrogram that have a frequency shift that exceeds a previous shift in the same cycle by at least 75 Hz. The peaks are maximum peaks of their respective pulse cycles. A comparison is made, to a predetermined pulsatility threshold, of a ratio of the time span to the immediately above-mentioned number, to determine whether the vessel is an artery.

In one more sub-aspect, the identifying names which artery or vein the vessel is.

Details of the novel device, and its automatic blood-vessel identification, are set forth further below, with the aid of the following drawings, which are not drawn to scale.

DETAILED DESCRIPTION OF EMBODIMENTS

Figure 2:
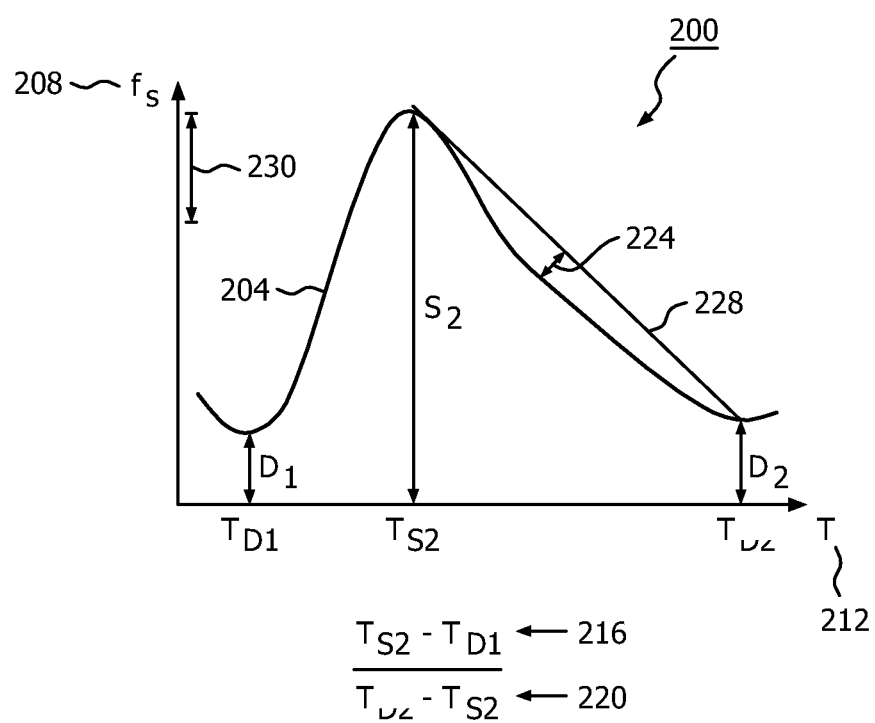
FIG. 2 is a graph of a pulse cycle, including features usable in classifying a blood vessel.

The description of what is proposed herein with regard to automated blood vessel identification is preceded with what largely is a review of the Doppler-based probe disclosed in the patent application "Automated Doppler Velocimetry Using a Low-Cost Transducer", the entire disclosure of which is incorporated herein by reference. Discussion focusing particularly on the present invention will then commence in connection with FIG. 2 and the subsequent figures.

Figure 1:
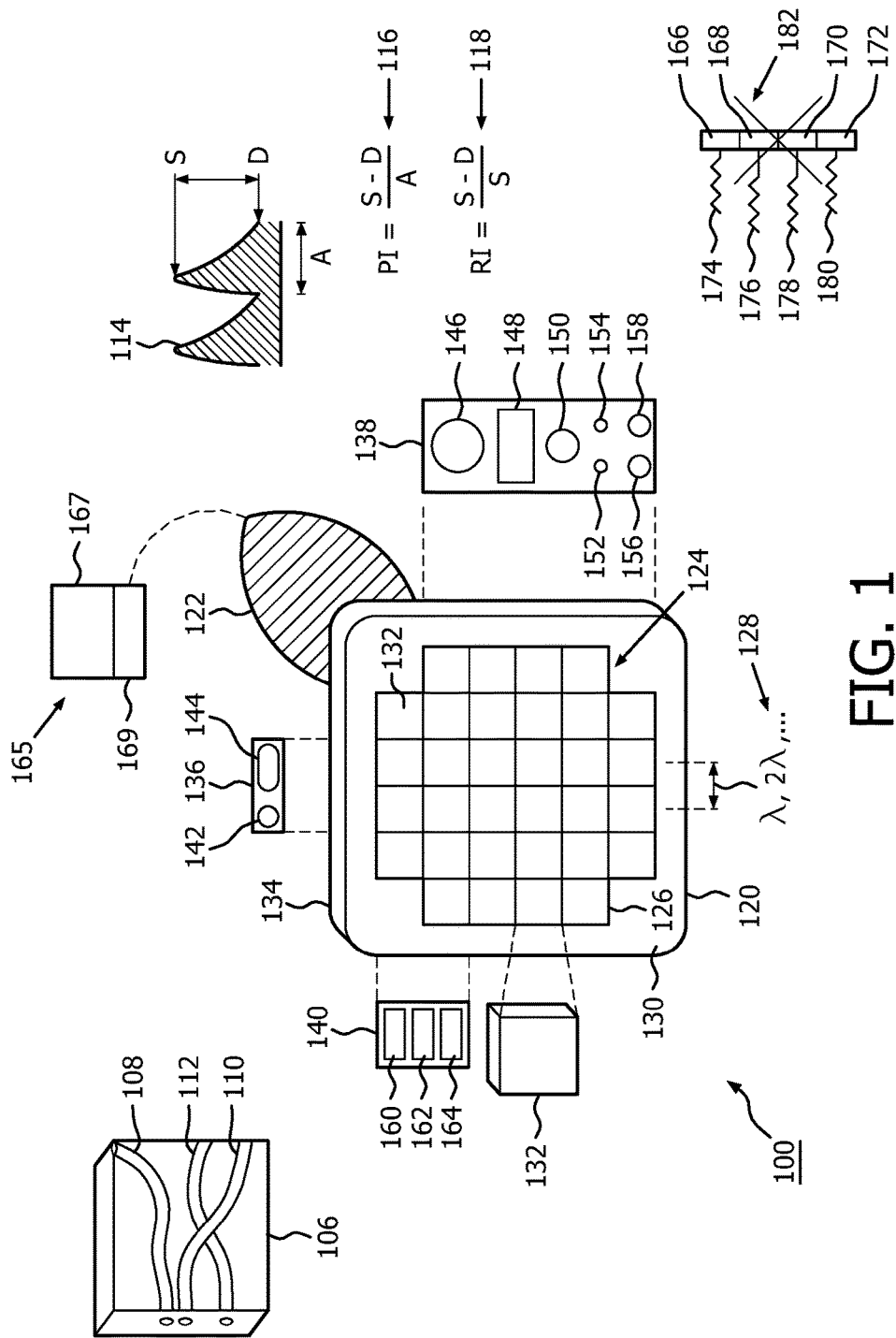
FIG. 1 is a schematic diagram showing, by example, an ultrasound probe, a volume of interest containing blood vessels, and a blood-flow waveform and respective clinical Doppler indices.

FIG. 1 depicts, by way of illustrative and non-limitative example, an ultrasound probe 100 and a volume or "volume of interest" 106 containing blood vessels 108, 110, 112. Further depicted are a blood-flow, or "spectral Doppler ultrasound", waveform 114 serving as an envelope of a spectrogram and respective clinical Doppler indices 116, 118.

The probe 100 is implementable as an automatic, handheld, stand-alone, self-contained, ultrasound examination device. It has a transducer housing 120 and a handle 122.

Within the transducer housing 120, a non-phased, two-dimensional transducer array 124 is comprised of transducer elements 126, the number of elements being determined by the scan volume and anatomy. Data acquisition occurs individually by element 126, although, as discussed in more detail further below, elements are operable concurrently to shorten the total acquisition time period.

As seen in FIG. 1 by way example, the number of elements 126 is 32. Thus, with an element size of 10 mm, an approximately 6 cm×6 cm volume is covered. Flush with a front surface 130 of the housing 120, are ultrasound-receiving faces or footprints 132 of the transducer elements 126, the same faces also transmitting, i.e., issuing, ultrasound.

The total of merely 32 elements 126 stands in stark contrast to the much greater number of elements that would be required in conventional medical imaging to cover the same 6 cm×6 cm volume.

In this regard, electronic focusing for medical imaging, as with a phased-array transducer, requires an inter-element spacing of a ½ wavelength, i.e., ½λ, or less. Doppler ultrasound for imaging can typically range from between $2 \times 10^6$ and $4 \times 10^6$ cycles per second (2 to 4 MHz). Ultrasound travels through soft body tissue at a speed of about 1540 meters/second. Wavelength, i.e., λ, is equal to velocity divided by frequency. Here, this is 1540 m/s divided by approximately $2 \times 10^6$ cycle/s=0.8 millimeter. Medical ultrasound imaging for a display would therefore require an inter-element spacing of less than 0.4 mm, and an element surface area of less than $(0.4 mm)^2$ which is less than 0.2 $mm^2$. Therefore, with a small element size on the order of ½λ, thousands of elements 126 would be required to build a 2D array that, like the one seen in FIG. 1, covers a volume of 6 cm by 6 cm.

The spacing (size) of elements in FIG. 1 is 10 mm, which, as discussed above, would ordinarily be more than 12λ of ultrasound used in examining the volume of interest 106 for the blood vessels 108, 110, 112 present.

More generally, the elements 126, in accordance with what is proposed herein, are spaced apart by more than ½λ, although inter-element spacing 128 may be λ, 2λ or more, as discussed hereinabove. The area of the face 132 is, correspondingly, at least 0.6 square millimeters ($mm^2$), and may be more, such as 10 $mm^2$, 25 $mm^2$, or 100 $mm^2$ as in FIG. 1.

Advantageously, the automatic ultrasound device 100 does not rely on display of medical images to reach a diagnosis; but, instead, features an array composed of fewer transducer elements and therefore fewer channels. Thus, cost of production is low, while, by virtue of automatic operation, reliability is maintained. Reliability may even be improved, as when medical examinations must be performed at a quicker pace. The automatic operation also tends to reduce examination time, thereby relieving workload, and making the examination more convenient.

During Doppler data acquisition, the elements 126 are fired either sequentially, or in one or more groups taking care that the acoustic signal from one element does not significantly affect others that are excited at the same time. For each element 126, the receive period lags the transmit period. The Doppler receive gate is correspondingly positioned in the receive period so as to enable sampling from a corresponding depth within the volume of interest 106.

On a back surface 134 of the housing 120, so as to face the user, are a number of user-interface, input-output panels which include a top panel 136, a left panel 138 and a right panel 140. An on-off switch 142 and an audio speaker face 144 are disposed in the top panel 136. The left panel 138 frames a function navigation/actuation button 146, a display 148, a Doppler power detection indicator 150, fetal heartbeat acquisition indicator 152, a maternal heartbeat acquisition indicator 154, a normal blood-flow indicator 156, and an abnormal blood-flow indicator 158. The right panel 140 includes three initializing-parameter-entry feedback windows 160, 162, 164.

Optionally, as indicated in FIG. 1 by the broken line, the probe 100 is connected, by wire or wirelessly, to a separate user interface 165 having a display device 167 and user-actuatable controls 169. A touch-sensitive feature for the screen of the device 167 can be included among the controls 169, as can other navigation and selection devices such as a mouse, buttons, keys slides, knobs and trackballs.

Within the optionally standalone probe 100, control circuitry (not shown), serving as the device proposed herein, can take the form of one or more integrated circuits (ICs), implementable in the transducer driving electronics. The one or more ICs can, alternatively, be configured for installation into existing apparatus such as ultrasound Duplex scanners.

The elements 126 of the array 124 all are operated to image independently.

This stands in contrast to phased arrays for example, which use multiple separate transducer elements collectively to image or steer a beam. In phased arrays, the steering and focusing is performed by appropriately delaying the input and/or output of elements with respect to other elements.

In accordance with what is proposed herein, the transducer elements of a group are fired simultaneously. The group elements continue imaging concurrently, and independently by element, until expiration of the group's data acquisition time period.

A device for the imaging by groups is configured not to collectively use any of the elements 126 to focus, nor to steer, a beam used in the imaging. By way of demonstration, the transducer elements 166, 168, 170, 172 in FIG. 1 each have their respective signals 174, 176, 178, 180. The signals 174, 180 on transmit lag the transmission signals 176, 178 thereby resulting in focus and/or steering of a resultant ultrasound beam. The probe is not implemented for such a protocol, as indicated by the "X" 182 in FIG. 1. Likewise, on receive, no delay is differentially applied to the elements 166, 168, 170, 172.

The description herein is of a non-phased, two-dimensional transducer array 124, although phased arrays, and transducer arrays of any other known and suitable architecture, are within the intended scope of the invention.

Clinical Doppler indices, such as the pulsatility index (PI) 116 and the resistance index (RI) 118 are Doppler angle-independent measures of blood pulsatility. The symbols S, D and A annotating the blood-flow waveform 114 in FIG. 1 represent, respectively, the peak systolic frequency shift, the end diastolic frequency shift, and the length of one cardiac cycle. The blood-flow waveform 114 is a graph of Doppler frequency, and thus blood flow velocity, versus time.

The probe 100 can utilize features of the waveform 114, such as both indices PI and RI, and their constituent caliper measurements S, D, and A, in identifying blood vessels 108-112 and in assessing normality of blood flow. Other features of the waveform 114 usable in the identifying are now mentioned with reference to FIG. 2.

A pulse cycle 200 is shown, represented by a waveform 204 whose units are frequency shift 208 over time 212. Its peak systolic frequency shift $f_s$ is denoted $S_2$ in FIG. 2, and its end diastolic frequency shift is $D_2$. The time to peak systole 216 is herein defined as the time period between $S_2$ and $D_1$ i.e., $T_{S2}$-$T_{D1}$. The time from peak systole to end diastole 220 is herein defined as $T_{D2}$-$T_{S2}$. Holder's defect 224 is defined as the maximum distance 224 between the waveform 204 and a straight line 228 between peak systole and end diastole. Another feature is the existence of periodic pulsatile flow in both the positive and negative channels of an artery, which is discussed in further detail in connection with FIG. 4 below. The ratio $(T_{S2}$-$T_{D1})/(T_{D2}$-$T_{S2})$ is also a feature usable in the identifying, as are other combinations of the above-mentioned features.

These features of the waveform 204 are examples of derived spectral characteristics usable in classifying and naming the vessel 108-112 under consideration by means of classifier implementable as a k-nearest neighbor (K-NN) classifier, with K=3 for example. Various feature inputs to the K-NN classifier, such as the PI, are used, each of the M types of input corresponding to a dimension in M-dimensional feature space. Another type of input to the classifier is training examples. Each training example corresponds to an actual clinical case, and includes the M feature inputs for that case, defining the example as a particular point, i.e., "example point", in the M-dimensional space, or "multi-dimensional feature space." With each example point is associated the respective outcome of "maternal artery" or "fetal artery", depending upon whether that training example actually pertained to a maternal artery or to a fetal artery. The outcome is known as the "ground truth." The classifier having been initialized with the training examples, a point in M-dimensional space is formed using the feature inputs derived for the blood vessel 108-112 currently being classified. For K=3, the 3 closest neighbor (example) points are identified. Each neighbor will have as its outcome either one possible classification outcome or the other. The majority vote prevails. There are never any ties since 3 is an odd number. Thus, the anatomical identifying is based on proximity in multi-dimensional feature space. The distance serving as a measure of similarity can be Euclidean, Manhattan, Bhattacharyyan, etc. Nearest neighbor classifiers, like the K-NN classifier, enjoy the benefit of simplicity. However, other alternative methods such as neural networks, or support vector machines (SVMs), could be used instead.

The vessel 108-112 is initially identified anatomically by classifying it as either an artery or a vein. This can be done without need for the K-NN classifier.

Figure 3:
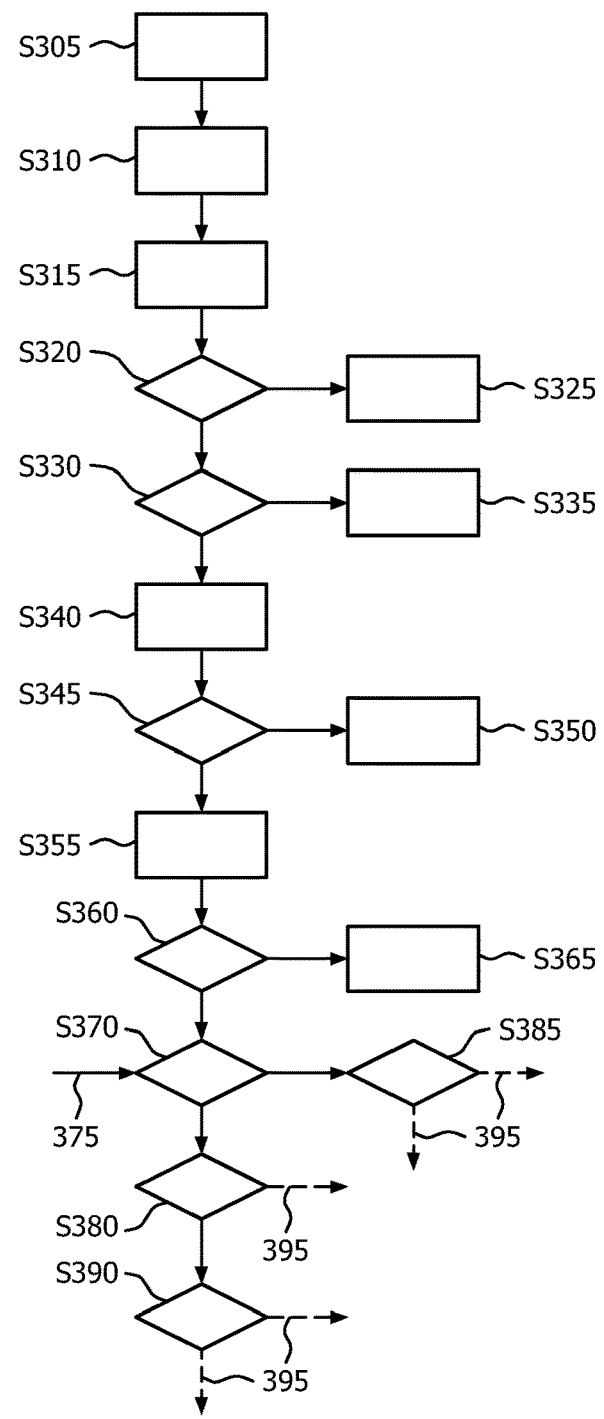
FIG. 3 is a flow chart for anatomically identifying a blood vessel.

FIG. 3 is an exemplary method 300 for, based on a spectrogram, anatomically identifying a blood vessel 108-112. The technique is based upon detecting the pulsatile flow characteristic of an artery. First, the maximum frequency envelope 204 is generated for the spectrogram (step S305). It is the envelope of the maximum frequency. Blood flow varies cross-sectionally in a vessel, with the blood near the vessel wall moving slower. The slower movement results in lower frequency shift components in the spectrum. Next, the number of significant peaks is computed (step S310). A peak is characterized by having lower points of the waveform 204 around it. A significant peak, i.e., the maximum peak of the cycle 200, is a peak of the maximum frequency envelope that is maximal and is preceded to the left by a value lower by DELTA 230. DELTA 230 is at least 75 Hz. In an FFT based sonogram, obtained with a 21 millisecond Hamming window using N=256 data points and a 50% overlap for the Doppler frequency shifts, for a sampling frequency of 44.1 KHz, DELTA 230 is 87.8 Hz. Step S315, which can be performed before or after step S310, is to compute the time span in seconds of the spectrogram. If the time span is less than a spectrogram size threshold (step S320), the spectral data acquired is deemed to be of bad quality, and acquisition by the probe 100 is re-executed (step S325). If, on the other hand, the time span meets the spectrogram size threshold (step S320), query is made as to whether the number of significant peaks computed in step S310 is greater or equal to a peak counting threshold (step S330). If the number is less than the peak counting threshold (step S330), the vessel 108-112 is determined to be a vein (step S335). If, however, the number is greater or equal to the peak counting threshold (step S330), a ratio is computed (step S340). The ratio is of the time span to the number of significant peaks. If the ratio is not within a predetermined range of a pulsatility metric (step S345), the signal is regarded as coming from a vein, or is a bad artery signal. Thus, Doppler data is re-acquired in this event (step S350). Otherwise, if the ratio is within the predetermined range (step S345), the signal is deemed indicative of an artery (step S355).

If the vessel is an artery (step S355), and the cardiac cycle length $T_{D2}$-$T_{D1}$ is between 0.3 and 0.6 seconds (step S360), the vessel is deemed to be a fetal artery (step S365).

Otherwise, if the length is outside that range (S360), the decision is made by a blood vessel classifier (S370). Classifier inputs from the user include: the gestational age; a rough, approximate location of the probe on the mother's abdomen; and training examples 375 in M-dimensional feature space.

Other inputs come directly or indirectly from the pulse-echo information from received ultrasound. Directly from the ultrasound, an average reflective index estimation is made for the tissue around the probe 100. This index is compared to a pre-defined reflection index list to determine the position of the probe 100 on the mother's body. Indirect inputs are the spectral information derived from the Doppler signal.

If the K-NN classifier is utilized in determining whether the vessel is maternal or fetal (step S370), and if the blood vessel is found to be a maternal artery, a determination is made as to whether it is a uterine artery (step S380). If, on the other hand, the vessel is found to be a fetal artery, a determination is made by the K-NN classifier as to whether it is the umbilical artery (step S385).

If the artery is found not to be the uterine artery (step S380), a determination is made as to whether the artery is the external iliac artery (step S390). This latter determination is made by means of an evidence-based model, as described herein below in connection with FIG. 4.

Further distinctions, as indicated in FIG. 3 by the broken line arrows 395, made in naming a vessel 108-112 according to the method 300 invoke the K-NN classifier. The vessel 108-112 is thereby anatomically identified by name, rather than merely by category.

Figure 4:
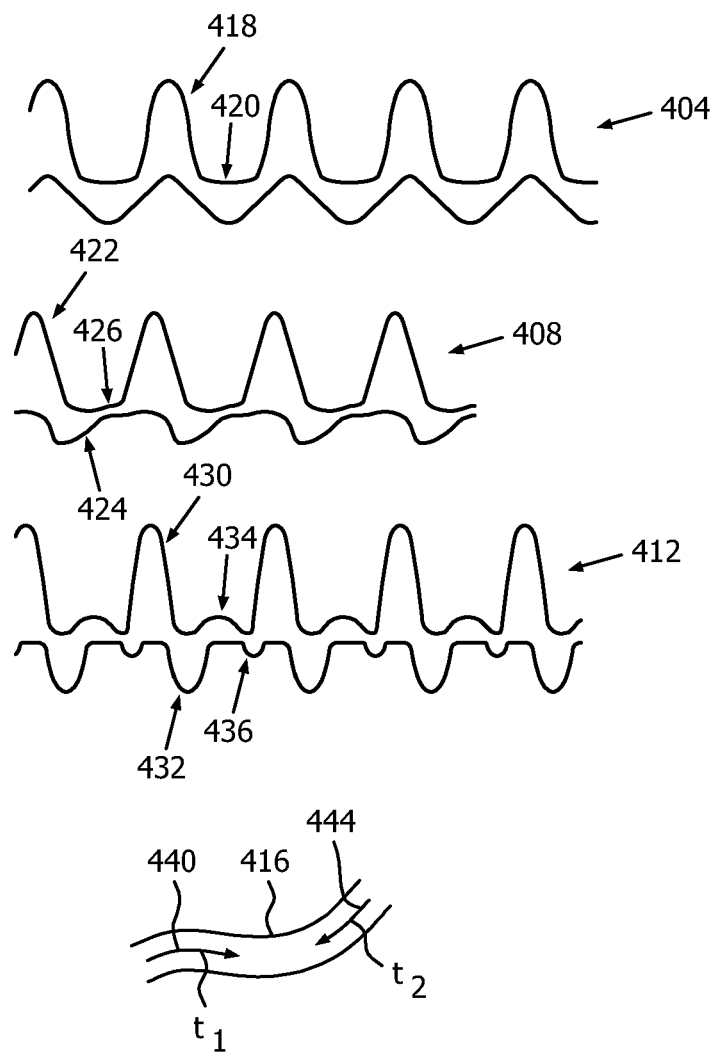
FIG. 4 is graphic representation of spectra of the external iliac artery, and channels of the artery.

FIG. 4 depicts examples of spectrograms 404, 408, 412 of the external iliac artery 416, and further shows representations of positive- and negative-flow channels 420, 424 of the external iliac artery. The external iliac arteries 416 are typically the biggest in the area probed. However, it can exhibit multiple forms of behavior, making it challenging to identify. The first spectrogram 404 is biphasic. It has a first of two phases 418, and a second of two phases 420. The second spectrogram 408 is triphasic, with three phases 422, 424, 426. The third spectrogram 412 is quadraphasic, with four phases 430, 432, 434, 436. The negative phases 420, 424, 432, 436 indicate a change in direction of blood flow, e.g., from a positive direction 440 at one time $t_1$ to a negative direction 444 at an immediately future time $t_2$. Blood flow is these directions 440, 444 occurs respectively in a positive-flow channel and a negative-flow channel. In the external iliace artery 416, periodic pulsatile flow occurs in both channels. This characteristic distinguishes the external iliac artery 416 from any other peripheral arteries in the region of insonation. Thus, a spectrogram resembling the spectrograms 404, 408, 412, the external iliac artery 416 provides evidence that the artery is the external iliac artery 416.

Another piece of evidence is the ratio 232 of time to peak systole 216 to the time from peak systole to end diastole 220. A lesser ratio favors the conclusion that the vessel is the external iliac artery 416.

Both piece of evidence may be weighted in an expression whose value is compared to a threshold to decide whether a conclusion that the artery is the external iliac artery 416 is warranted. The weights are estimated for these two piece of evidence, and for any further types of evidence, based on the number of occurrence of the evidences in the training data.

Figure 5:
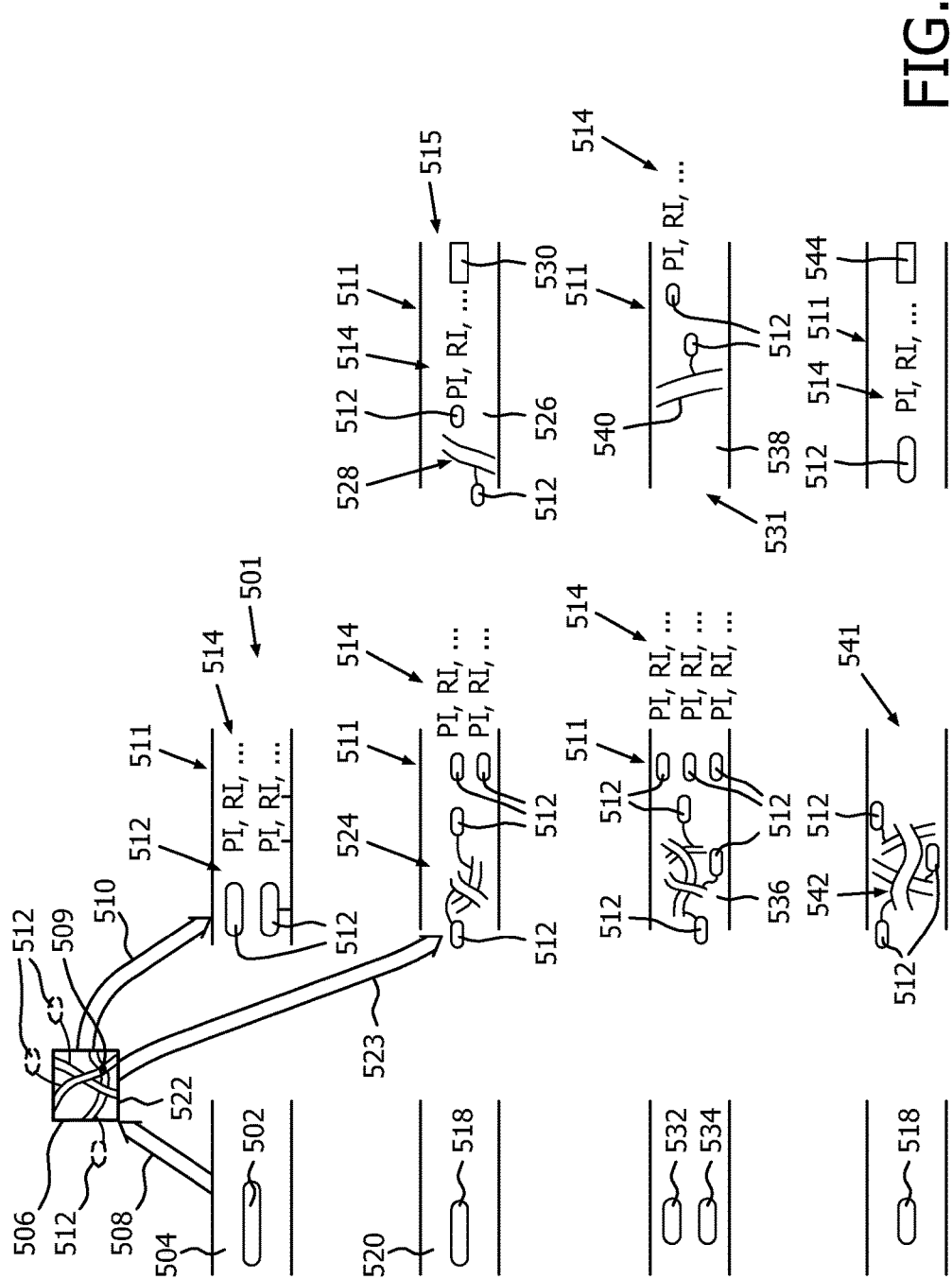
FIG. 5 is a conceptual view of user interaction with regard to the automatic naming of a blood vessel and clinical diagnostic support.

FIG. 5 demonstrates, by way of illustrative and non-limitative example, implementations offering interactive user interface, automatic vessel naming and graphic display.

In a first design 501, a user-selectable button 502 designating "all vessels" is shown on a screen 504 of the display device 167. Pressing the button 502 launches a process by which all vessels 108-112 in the region of insonation are interrogated. Based on the information acquired by means of the interrogation, a spatial map 506 of vessels is generated. It includes all vessels 108-112 in the region having more than a minimum size. Generation of the map 506 is indicated by the arrow 508. It is generated by determining for each transducer element 126, whether each voxel 509 under its footprint 132 has vessel flow information. Based on the map 506 and responsive to its generation, as indicated by the arrow 510, each vessel in the map is anatomically identified concurrently, in a table 511, by name 512, e.g., "midcerebral artery", the respective name being shown on the screen 504 for each vessel named. Alongside each named vessel 108-112, in the table 511, are displayed Doppler indices 514, such as PI and RI whose values pertain to the vessel. Since "all vessels" was the selection, each named vessel 108-112 is interrogated again for the spectral information needed to derive the Doppler indices 514 to be displayed on the screen 504. Alternatively, the second interrogation can be foregone, if the first interrogation for generating the map yielded sufficient spectral information and that information has been retained in storage for re-access. On the other hand, for example, the Doppler signals from first interrogation may not have been used to generate spectrograms, since Doppler power may be calculated in the time domain. This is described in the commonly-owned patent application by the same inventors entitled "Time-Domain Doppler-Power Computation Based Vessel-Localization", the entire disclosure of which is incorporated herein by reference.

In a second design 515, the droplist item selected is an anatomical description, i.e., a set 518, that may include a vessel name, a vessel category, or some combination, such as "only umbilical artery", "artery+vein", "only vein", "uterine+external iliac", etc. Information only pertaining to the selected anatomical description 518 is fetched, based on the map 506, for display onscreen 520. The dashed circle 522, overlaid on the map 506 here for illustrative purposes, and the arrow 523 stemming from the circle, signify that only the vessels 108-112 in that part of the map are interrogated. Based on this second interrogation, an image 524 of the vessels called for in the set 518 is rendered onscreen 520, the vessel names 512 are shown, and the Doppler indices 514 are shown as well. The image 524 may likewise be annotated by the respective vessel names 512. Display of the image 524 is primarily for the benefit of the specialist, and this feature may be bypassed for the general practitioner. A further screen 526 may be brought up to zoom in on, or enlarge, the image 524. This is triggerable on a touch screen by touching a desired vessel in the image 524, its annotating name 512 or respective indices 514. As a result, an enlarged image 528 is shown on the screen 526, along with the name 512 and indices 514. In addition, a diagnosis 530 of "normal" or "abnormal" is rendered as part of the clinical decision support, "normal" indicating normal blood flow for the vessel 108-112 and "abnormal" indicating abnormal blood flow. In particular and by way of example, the Doppler parameters are compared with nomograms, i.e., tables representing the range of expected Doppler indices as a function of gestational age, to determine whether the flow profile is normal or abnormal.

In a third design 531, two separate items 532, 534, such as "artery" and "vein", are selected. The resulting screen 536 resembles the onscreen display 520 of the second design 515. Further user selection from the resulting screen 536, causes a screen 538 to show a zoomed image 540 and the other onscreen items of the screen 526 of the second design 515, except that no diagnosis is rendered.

In a fourth design 541, selection of a set 518 brings up an annotated image 542 of vessels 108-112. Further selection on an annotation 512, or on the vessel 108-112 itself, displays again the vessel name 512 and indices 514. It also display a diagnosis 544 of normality/abnormality.

Figure 6:
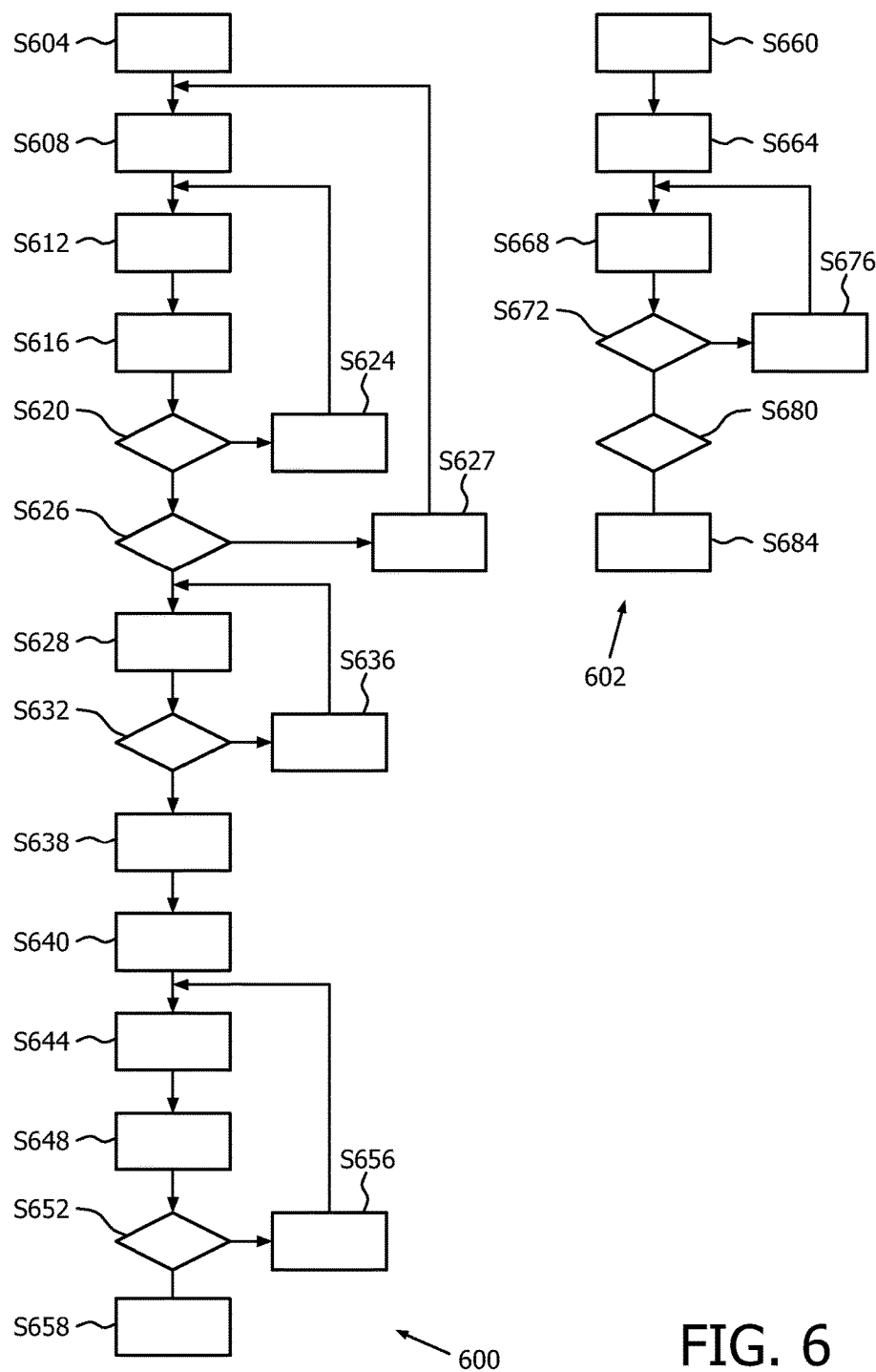
FIG. 6 is a pair of flow charts of the process by which that automatic blood vessel naming device operates, and interacts with the user.

Exemplary processes 600, 602 for automatically labeling blood vessels are seen in FIG. 6. The probe 100 is set on an anatomical region to interrogate it for all vessels of a size greater than a minimum (step S604). Processing points to the transducer elements 126 of a current group of the elements (step S608). Processing further points to current voxels 509 under the respective footprints 132 of the current elements 126 (step S612). By ultrasound, Doppler shift information is acquired from the current voxels 509 (step S616). If there are any remaining voxels 509 from which Doppler information has not been acquired (step S620), next voxels serve as the current voxels (step S624) in a return to step S612. When no voxels 509 remain for the current group (step S620), query is made as to whether a next group exists (step S626). If one exists (step S626), the next group is made the current group (step S627) and processing branches back to step S608. When the groups are all processed (step S626), the Doppler power is computed for the current voxel 509, based on the ultrasound-borne signal detected by the element 125 overriding the voxel (step S628). If a next voxel 509 exists (step S632), that next voxel serves as the current voxel (step S636) in a return to step S628. When no voxel 509 remains (step S632), vessel map generation begins, based on the Doppler powers computed for voxels of sufficient blood flow that offer sufficient coverage of the vessel 108-112 exhibiting the flow (step S638). The vessel information in the map 506 is image-wise segmented into separate vessels 108-112 (step S640). This can be done as follows. A 6×6×50 matrix is constructed, corresponding to the 6 rows of elements 126, the 6 columns of elements, and 50 layers at a depth of 2 mm per layer. Referring back to FIG. 1, the four corner elements 126 are missing. Thus, the 32×50=1600 matrix entries correspond to the 1600 voxels interrogated. If flow is detected, the entry is "1"; otherwise, it is "0." Under a nearest-neighbor criterion, two "1" entries within the same layer are deemed part of the same vessel 108-112 if they are immediately adjacent in the checkerboard sense, i.e., laterally or diagonally. For each section of adjacent entries within a layer, the centroid is calculated. If centroids of adjacent layers meet a proximity criterion, the voxels 509 or their sections are considered to be part of the same vessel 108-112. Separate vessels can be joined if they have respective endpoint voxels 509 within sufficient proximity, the signals of the two voxels being sufficiently correlated. Next, in the process 600, flow characteristics are derived for the current vessel 108-112 (step S644). The vessels 108-112 in the map 506 are individually, anatomically named based on the derived characteristics (step S648). If a next vessel 108-112 exists (step S652), it is deemed now the current vessel (step S656) with a return to step S644. Otherwise, if a next vessel 108-112 does not exist (step S652), the map is complete (step S656).

In the related, user-interactive process 602, the user launches vessel/category selection(s) in conjunction with operating controls 502, 516, 532, 534 (step S660). A sample volume 509 is automatically set for the current vessel 108-112 based on the map 506 whose generation was completed in step S656 and on the selection(s) in step S660 (step S664). The sample volume 509 is interrogated (step S668). If a next voxel 509 exists (step S672), return is made to step S668 with that next voxel serving as the current sample volume (step S676). Otherwise, if no voxel 509 remains (step S672), Doppler indices 514 are derived based on the interrogations in step S668 (step S680). The indices 514 are displayed (step S684). The interrogation in step S668 need not be confined to a single voxel 509—when elements 126 are fired in groups, a number of sample volumes are interrogated concurrently.

A device is configured for interrogating a blood vessel to derive flow characteristics and for, responsive to the deriving and based on the derived characteristics, anatomically identifying the vessel. A spatial map of the vessels may be generated based on the interrogating, and specifically the Doppler power computed from data acquired in the interrogating. Subsequent interrogating may occur, based on the map and on a user-selected set of vessels and/or vessel categories, to derive clinical Doppler indices. The device can be designed to automatically set a sample volume for the subsequent interrogating, and to operate automatically from the user selection to display of the indices. The display may further include an image of the vessels summoned by the set, annotated by their individual anatomical names, and optionally a diagnosis relating to blood flow. The displayed image may be enlarged to zoom in on the user's onscreen selection. The device may feature a two-dimensional ultrasound non-phased array of transducer elements.

Although methodology of the present invention can advantageously be applied in providing medical diagnosis for a human or animal subject, the scope of the present invention is not so limited. More broadly, techniques disclosed herein are directed to efficiently finding, and subjecting to fluid-flow analysis, vessels in body tissue, in vivo, in vitro or ex vivo.

Applications include carotid and renal arteries screening, ABI measurements for detecting peripheral arterial disease (PAD), transcranial, bleed detection in trauma or other hemorrhages in addition to fetal well-being assessment.

While the invention has been illustrated and described in detail in the drawings and foregoing description, such illustration and description are to be considered illustrative or exemplary and not restrictive; the invention is not limited to the disclosed embodiments.

For example, the first design 501 may incorporate the diagnosis 530 of the second design 515.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. Any reference signs in the claims should not be construed as limiting the scope.

A computer program can be stored momentarily, temporarily or for a longer period of time on a suitable computer-readable medium, such as an optical storage medium or a solid-state medium. Such a medium is non-transitory only in the sense of not being a transitory, propagating signal, but includes other forms of computer-readable media such as register memory, processor cache and RAM.

A single processor or other unit may fulfill the functions of several items recited in the claims. The mere fact that certain measures are recited in mutually different dependent claims does not indicate that a combination of these measures cannot be used to advantage.

What is claimed is:

1. A system configured to anatomically identify a blood vessel, the system comprising:
a non-phased array of ultrasound transducers having an inter-element spacing of more than an ultrasound wavelength ($\lambda$) apart from one another; and
one or more processors configured by machine-readable instructions to:
generate, via concurrent operation of two or more ultrasound transducers of the non-phased array of ultrasound transducers, a spatial map of one or more blood vessels, the one or more blood vessels including a first blood vessel;
determine, based on the spatial map, pulsatile flow characteristics of the first blood vessel;
identify, based on the pulsatile flow characteristics of the first blood vessel, a blood vessel type of the first blood vessel, wherein identification comprises determining whether the first blood vessel is a vein or an artery;
assign, based on the blood vessel type and a location of the first blood vessel, a name to the first blood vessel, wherein, responsive to the blood vessel type being a first named artery, assigning the name comprises classifying the first named artery with a k-nearest neighbor classifier;
obtain a user input via a user interface; and
cause the first blood vessel and the name assigned to the first blood vessel to be presented on the user interface based on a determination that the first blood vessel corresponds to the user input.

2. The system claim 1, wherein the one or more processors are further configured by machine-readable instructions to:
determine periodic pulsatile motion in both a positive-flow channel and a negative-flow channel of the first named artery; and
classify the first named artery based on determining the periodic pulsatile motion in both the positive-flow channel and the negative-flow channel of the first named artery.

3. The system of claim 1, wherein the inter-element spacing of the non-phased array of ultrasound transducers is more than two ultrasound wavelength ($\lambda$).

4. The system of claim 1, wherein the inter-element spacing of the non-phased array of ultrasound transducers is at least 10 mm.

5. The system of claim 1, wherein determining the pulsatile flow characteristics of the first blood vessel comprises:

generating a maximum frequency envelope for a spectrogram based on an output of the non-phased array of ultrasound transducers; determining a number of significant peaks in the maximum frequency envelope; determining a time span of the spectrogram; and determining a ratio of the time span to the number of significant peaks, and wherein identifying the blood vessel type comprises identifying the first blood vessel type as an artery when the ratio is within a predetermined range of pulsatility metric and identifying the first blood vessel type as a vein when the ratio is not within the predetermined range of pulsatility metric.

6. The system of claim 5, wherein the one or more processors are further configured by machine readable instructions to:

determine a cardiac cycle length;
compare the cardiac cycle length to a predetermined threshold; and
classify, based on the comparing, the artery.

7. The system of claim 1, wherein the non-phased array of ultrasound transducers is configured to not collectively use of ultrasound transducers to focus or steer a beam during use of the ultrasound transducers to interrogate the first blood vessel to determine the pulsatile flow characteristics of the first blood vessel.

8. The system of claim 1, wherein the one or more processors are further configured by machine readable instructions to:

determine, based on the spatial map, one or more Doppler parameters for the first blood vessel;
determine a normality of blood flow in the first blood vessel by comparing the one or more Doppler parameters with a range of expected Doppler indices as a function of gestational age;
determine, based on the normality of blood flow, a diagnosis for the first blood vessel; and
display the one or more Doppler parameters and the diagnosis for the first blood vessel on the user interface.

9. The system of claim 1, wherein the pulsatile flow characteristics comprise periodic pulsatile flow that occurs in both positive-flow and negative-flow channels.

10. The system of claim 1, wherein the user input relates to one or both of a blood vessel's type or a blood vessel's name, and wherein displaying the first blood vessel and the name assigned to the first blood vessel comprises displaying the first blood vessel and the name assigned to the first blood vessel on the user interface when the user input corresponds to one or both of a type of the first blood vessel or the name assigned to the first blood vessel.

11. A method for anatomically identifying a blood vessel with a system, the system including (i) a non-phased array of ultrasound transducers having an inter-element spacing of more than an ultrasound wavelength ($\lambda$) apart from one another and (ii) one or more processors, the method comprising:

generating, via concurrent operation of two or more ultrasound transducers of the non-phased array of ultrasound transducers, a spatial map of one or more blood vessels, the one or more blood vessels including a first blood vessel;
determining, with the one or more processors and based on the spatial map, pulsatile flow characteristics of the first blood vessel;
identifying, with the one or more processors and based on the pulsatile flow characteristics of the first blood vessel, a blood vessel type of the first blood vessel, wherein the identification comprises determining whether the first blood vessel is a vein or an artery;
assigning, with the one or more processors and based on the blood vessel type and a location of the first blood vessel, a name to the first blood vessel, wherein, responsive to the blood vessel type being a first named artery, assigning the name comprises classifying the first named artery with a k-nearest neighbor classifier;
obtaining, with the one or more processors, a user input via a user interface; and
causing, with the one or more processors, the first blood vessel and the name of the first blood vessel to be displayed on the user interface based on a determination that the first blood vessel corresponds to the user input.

12. The method of claim 11, further comprising:
determining, with the one or more processors, periodic pulsatile motion in both a positive-flow channel and a negative-flow channel of the first named artery; and
classifying, with the one or more processors, the first named artery based on determining the periodic pulsatile motion in both the positive-flow channel and the negative-flow channel of the first named artery.

13. The method of claim 11, wherein the inter-element spacing of the non-phased array of ultrasound transducers is more than two ultrasound wavelength ($\lambda$).

14. The method of claim 11, wherein the inter-element spacing of the non-phased array of ultrasound transducers is at least 10 mm.

15. The method of claim 11, wherein determining the pulsatile flow characteristics of the first blood vessel comprises: generating a maximum frequency envelope for a spectrogram based on an output of the non-phased array of ultrasound transducers; determining a number of significant peaks in the maximum frequency envelope; determining a time span of the spectrogram; and determining a ratio of the time span to the number of significant peaks, and wherein identifying the blood vessel type comprises identifying the first blood vessel type as an artery when the ratio is within a predetermined range of pulsatility metric and identifying the first blood vessel type as a vein when the ratio is not within the predetermined range of pulsatility metric.

16. The method of claim 15, further comprising:
determining, with the one or more processors, a cardiac cycle length;
comparing, with the one or more processors, the cardiac cycle length to a predetermined threshold; and
classifying, based on the comparing, the artery.

17. The method of claim 11, wherein the non-phased array of ultrasound transducers is configured to not collectively use of ultrasound transducers to focus or steer a beam during use of the ultrasound transducers to interrogate the first blood vessel to determine the pulsatile flow characteristics of the first blood vessel.

18. The method of claim 11, further comprising:
determining, with the one or more processors and based on the spatial map, one or more Doppler parameters for the first blood vessel;
determining, with the one or more processors, a normality of blood flow in the first blood vessel by comparing the one or more Doppler parameters with a range of expected Doppler indices as a function of gestational age;
determining, based on the normality of blood flow, a diagnosis for the first blood vessel; and causing, with the one or more processors, the one or more Doppler parameters and the diagnosis for the first blood vessel to be displayed on the user interface.

19. The method of claim 11, wherein the user input relates to one or both of a blood vessel's type or a blood vessel's name, and wherein the method further comprises causing, with the one or more processors, the first blood vessel and the first blood vessel's name to be displayed on the user interface when the user input corresponds to one or both of a type of the first blood vessel or the name assigned to the first blood vessel.

20. A system configured to anatomically identify a blood vessel, the system comprising:
   a non-phased array of ultrasound transducers having an inter-element spacing of more than a ultrasound wavelength ($\lambda$) apart from one another; and
   one or more processors configured by machine-readable instructions to:
      generate, via the non-phased array of ultrasound transducers, a spatial map of one or more blood vessels, the one or more blood vessels including a first blood vessel;
      determine, based on the spatial map, pulsatile flow characteristics of the first blood vessel;
      identify, based on the pulsatile flow characteristics of the first blood vessel, a blood vessel type of the first blood vessel, wherein identification comprises determining whether the first blood vessel is a vein or an artery;
      assign, based on the blood vessel type and a location of the first blood vessel, a name to the first blood vessel;
      obtain a user input via a user interface; and
      cause the first blood vessel and the name assigned to the first blood vessel 532 to be displayed on the user interface based on a determination that the first blood vessel corresponds to the user input.

21. The system of claim 20, wherein the non-phased array of ultrasound transducers comprise a plurality of rows of ultrasound transducers and a plurality of columns of ultrasound transducers,
   wherein the one or more processors are configured by machine-readable instructions to:
      obtain Doppler shift information via concurrent operation of the non-phased array of ultrasound transducers; and
      construct, based on the Doppler shift information, a multi-layer matrix having a plurality of layers to generate the spatial map such that the multi-layer matrix comprises matrix entries corresponding to regions of a subject, wherein each matrix entry of the matrix entries indicate whether flow was detected in the Doppler shift information for the respective corresponding region, wherein the spatial map comprises the multi-layer matrix, and wherein each layer of the plurality of layers corresponds to the plurality of rows of ultrasound transducers and the plurality of columns of ultrasound transducers; and
      determine, based on the multi-layer matrix, the pulsatile flow characteristics of the first blood vessel.

22. The system of claim 20, wherein the pulsatile flow characteristics comprises a maximum frequency envelope, a number of significant peaks, or periodic pulsatile flow occurs in both positive-flow and negative-flow channels.

* * * * *